United States Patent [19]

Harroff

[11] 4,013,070
[45] Mar. 22, 1977

[54] BODY PART IMMOBILIZER

[75] Inventor: Marlin R. Harroff, Bourbon, Ind.

[73] Assignee: Orthopedic Equipment Company, Inc., Bourbon, Ind.

[22] Filed: Jan. 27, 1976

[21] Appl. No.: 652,751

Related U.S. Application Data

[63] Continuation-in-part of Ser. No. 540,505, Jan. 13, 1975, Pat. No. 3,935,858.

[52] U.S. Cl. .................................. 128/80 C; 128/77
[51] Int. Cl.² .......................................... A61F 3/00
[58] Field of Search ................. 128/80 C, 133, 165, 128/DIG. 15, 80 R, 87 R

[56] References Cited

UNITED STATES PATENTS

| 3,232,289 | 2/1966 | Zimmerman | 128/DIG. 15 |
| 3,358,141 | 4/1965 | Hoffmann et al. | 128/DIG. 15 |
| 3,587,572 | 6/1971 | Evans | 128/80 C |
| 3,831,467 | 8/1974 | Moore | 128/80 C |
| 3,935,858 | 2/1976 | Harroff | 128/80 C |

OTHER PUBLICATIONS

Richards Orthopedic & Otological Instruments Catalogue of 1966, p. 17.

Primary Examiner—Lawrence W. Trapp
Attorney, Agent, or Firm—Oltsch & Knoblock

[57] ABSTRACT

A wraparound immobilizer for a body part of a patient, such as the knee, ankle or wrist, in which the inside and outside stays which assist in immobilizing the body part are adjustable to accommodate the size of the patient. Additionally, the stays may carry the attachment straps by which the immobilizer is secured about the body part.

11 Claims, 12 Drawing Figures

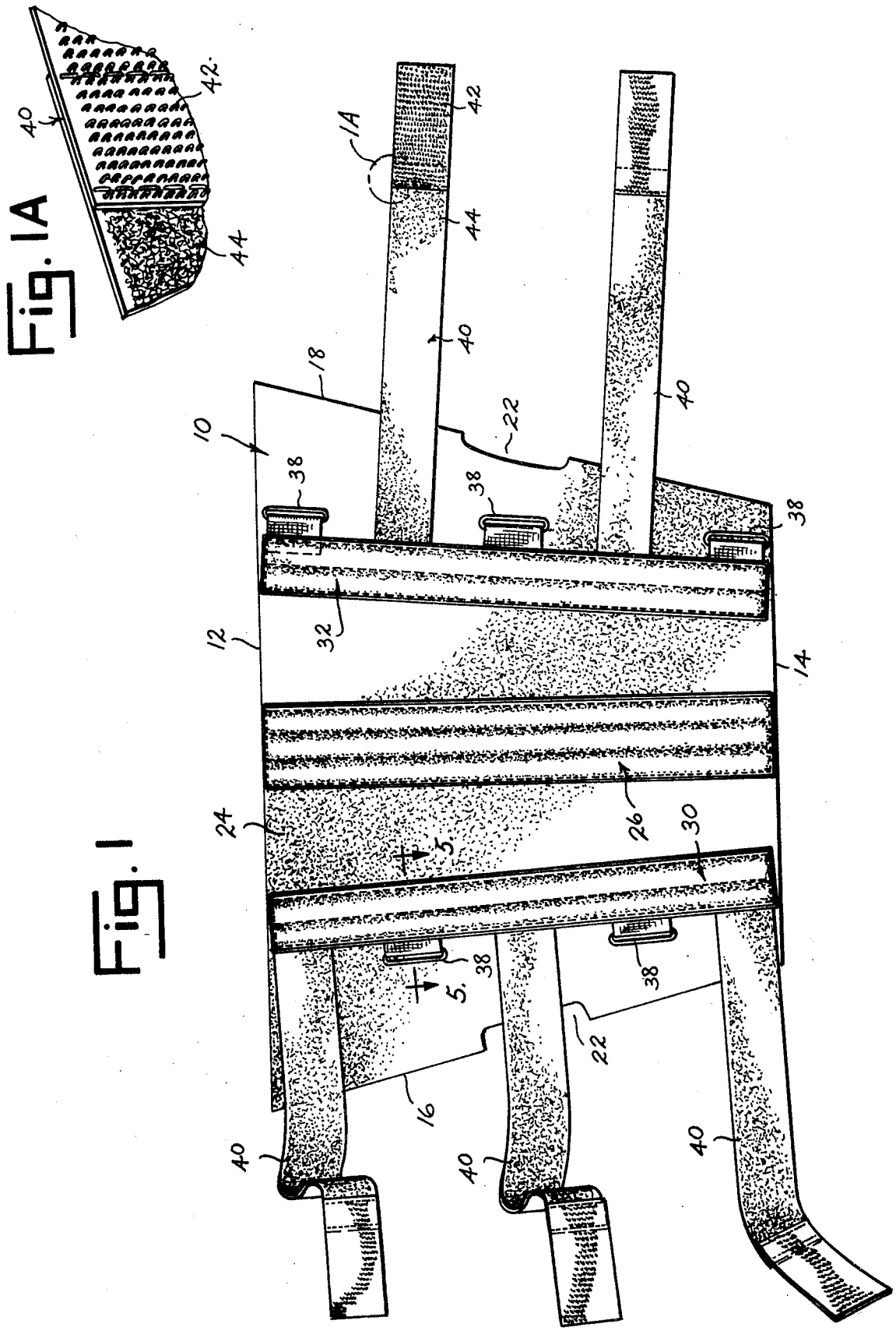

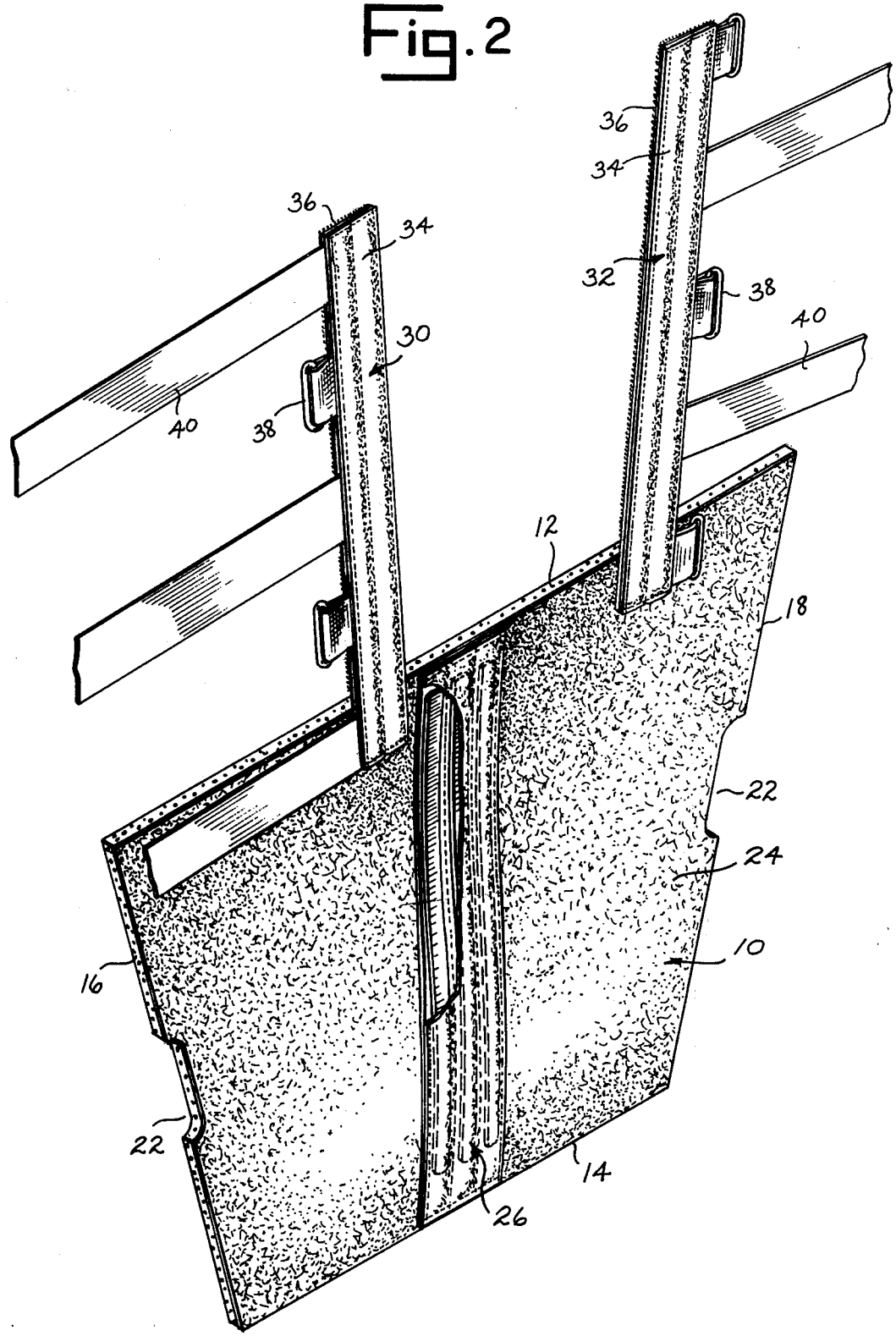

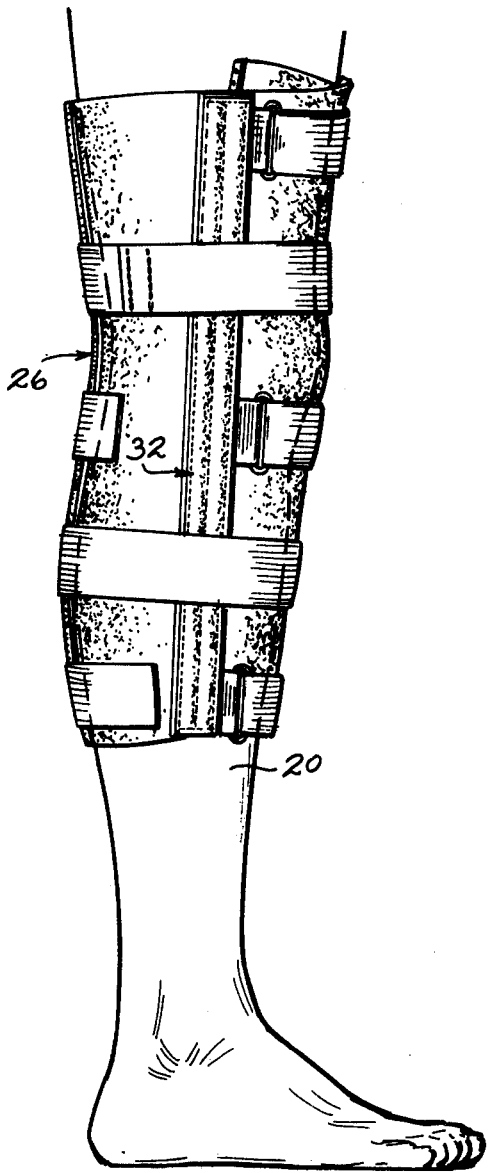
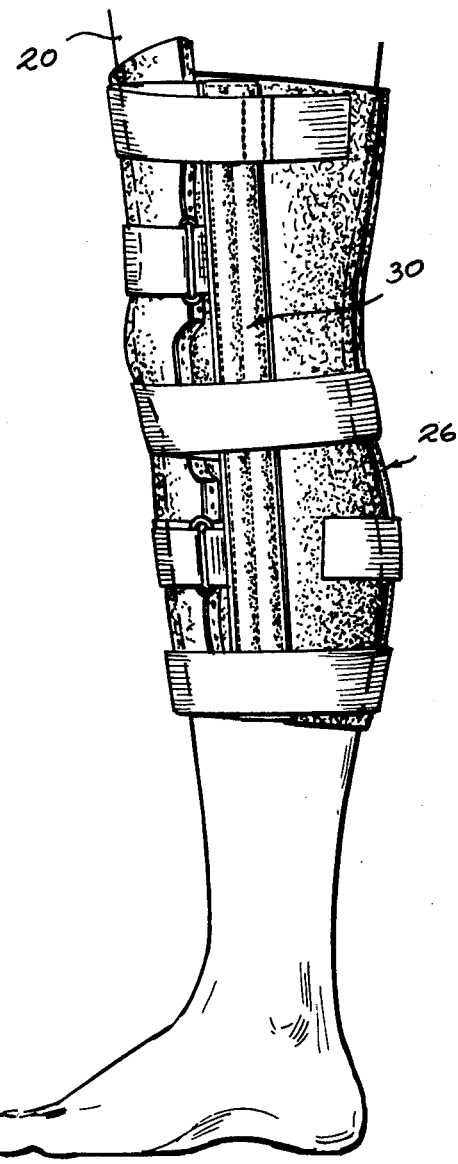
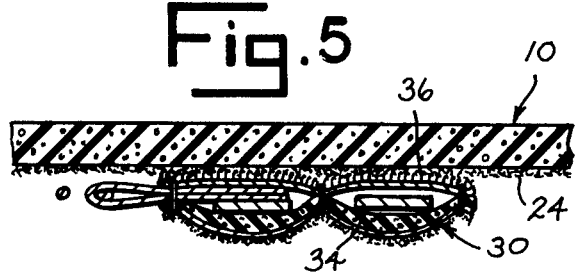

BODY PART IMMOBILIZER

CROSS REFERENCE TO A RELATED APPLICATION

This application is a continuation in part of application Ser. No. 540,505, filed Jan. 13, 1975 and now Pat. No. 3,935,858.

SUMMARY OF THE INVENTION

This invention relates to an orthopedic device for immobilizing a body part of a patient and will have specific but not limited application to a knee, ankle or wrist immobilizer which is of universal application to accommodate patients of varying size.

The immobilizer includes a flexible cover which extends around the body part of the patient. A pair of stays are detachably connected to the cover and positioned one on one side and one on the other side of the body part. The stays may also carry belts or similar securement means by which the cover of the immobilizer is secured about the body part. The position of the pair of stays by being detachably connected to the immobilizer cover can be varied so as to accommodate the particular size of the patient. Accordingly, it is an object of this invention to provide a body part immobilizer which is of universal application to accommodate patients of different size.

Another object of this invention is to provide a wrap-around immobilizer for the knee, ankle, wrist or other body part in which stays are adjustably applied to the cover of the immobilizer.

Still another object of this invention is to provide an immobilizer which is for a body part of a patient and which includes detachable stays positioned on the sides of the body part and carrying means for securing the cover about the body part.

Other objects of this invention will become apparent upon a reading of the invention's description.

BRIEF DESCRIPTION OF THE DRAWINGS

FIG. 1 is a plan view of a knee immobilizer shown in detached form.

FIG. 1A is a detailed view of that portion of FIG. 1 within broken line circle 1A.

FIG. 2 is a plan view of the knee immobilizer showing the stays thereof detached from the immobilizer.

FIG. 3 is a perspective view of the knee immobilizer shown applied about the knee of a patient and as viewed from one side.

FIG. 4 is also a perspective view of the immobilizer shown applied about the knee of the patient and viewed from the opposite side.

FIG. 5 is a fragmentary cross sectional view taken along line 5—5 of FIG. 1.

DESCRIPTION OF THE PREFERRED EMBODIMENTS

Figure 6:
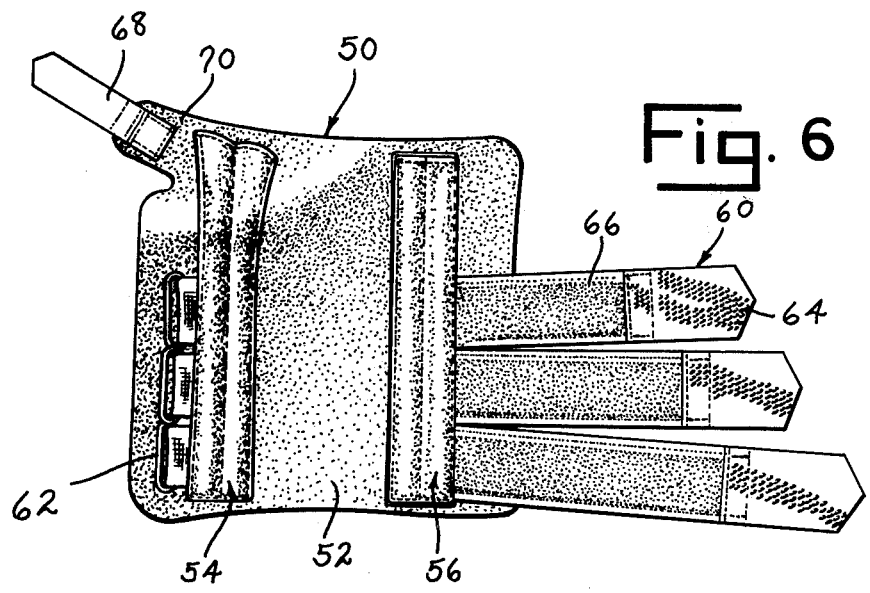
FIG. 6 is a plan view of a wrist immobilizer.

The preferred embodiments illustrated are not intended to be exhaustive or to limit the invention to the precise forms disclosed. They are chosen and described in order to best explain the principles of the invention and its application and practical use to thereby enable others skilled in the art to best utilize the invention.

The immobilizer shown in FIGS. 1–5 includes a flexible cover 10. Cover 10 includes an upper edge 12 and a parallel lower edge 14, as well as side edges 16 and 18. To accommodate the anatomical shape of a patient's leg 20, side edges 16 and 18 preferably taper from upper edge 12 to lower edge 14 with the cover assuming a trapezoidal appearance when in planar form. Also each side edge 16 and 18 may be formed with a cut-out 22 to accommodate the knee cap of the patient. Cover 10 may be formed of any one of a variety of materials, such as a polyvinyl foam construction, having a looped pile material 24 applied to its outer surface. A fixed stay 26 is positioned midway between side edges 16 and 18 and extends from upper edge 12 to lower edge 14 of the cover. Stay 26 is secured in position by being sewn or otherwise appropriately affixed to cover 10. Stay 26 is shaped to generally conform to the anatomical curvature of the back of the leg at the knee.

Also connected to cover 10 are a pair of detachable stays 30 and 32. Stays 30 and 32 are located to the inside and outside of the knee when the immobilizer is secured about the patient as shown in FIGS. 3 and 4. Each stay 30 and 32 includes an encasement 34 to which a plurality of hook or similar type securement members 36 are attached to one side. Hook members 36 are designed so as to engage and interlock with the loop pile material 24 of cover 10 and serve to connect stays 30 and 32 to the cover. Hook members 36 of stays 30 and 32 and loop pile material 24 of cover 10 may be of the cooperating interlocking type sold under the well known trademark "Velcro". Stays 30 and 32 are connected to cover 10 by having their hook members 36 pressed into engagement with loop pile material 24 of the cover. Rings 38 and straps 40 are also secured to stays 30 and 32 for the purpose of securing cover 10 about the knee of the patient.

In FIGS. 3 and 4 the immobilizer is shown attached to leg 20. Cover 10 is wrapped around the knee with stay 26 being positioned to the rear or back of the knee and with side edges 16 and 18 in a juxtaposed or overlapping arrangement, depending upon the size of the patient. Stays 30 and 32 are applied to the cover at selected locations on the inside and outside of the knee, thus providing lateral rigidity to the immobilizer. The free end portions of straps 40 are inserted through rings 38 and return bent so that the hook members 42 of each strap can be pressed into interlocking engagement with the pile material 44 extending along the remainder of the strap.

By utilizing loop pile material with cover 10 and hook member attachments with stays 30 and 32, the stays can be easily removed from and reapplied to the cover in adjusting the immobilizer to accommodate a particular size patient. The interlocking adherence between hook members 36 of stays 30 and 32 and the loop pile material of cover 10 is of sufficient strength to enable the cover to be secured about the patient's knee through the use of rings 38 and straps 40.

While it is preferred that stays 30 and 32 of the immobilizer also carry the means for securing cover 10 about the knee of the patient, it is to be understood that such securement means whether straps, rings or buckles can be sewn directly to cover 10 with detachable stays 30 and 32 serving only as rigidifying means.

Figure 7:
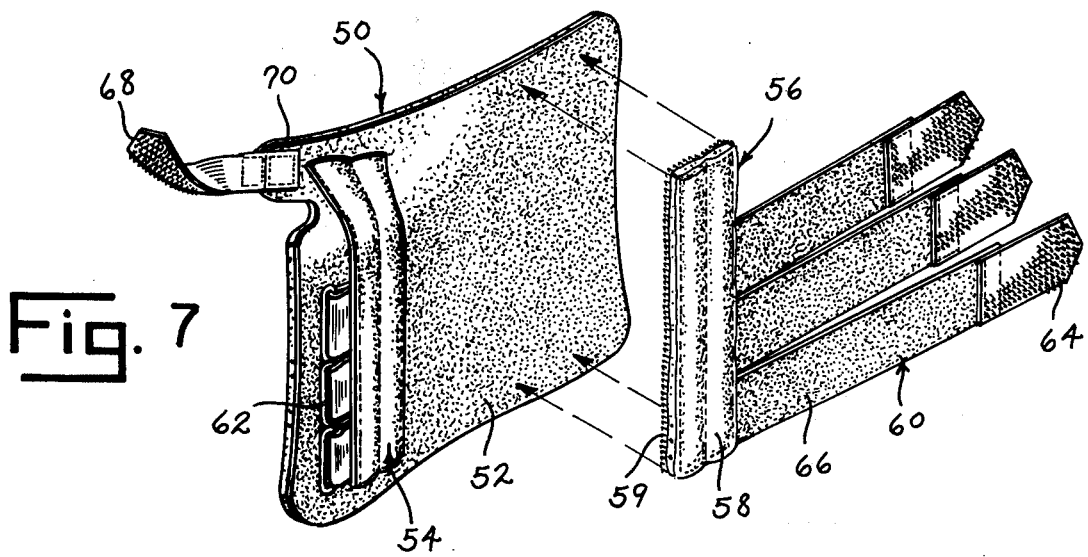
FIG. 7 is a plan view of the wrist immobilizer showing a stay thereof detached from the immobilizer.
Figure 8:
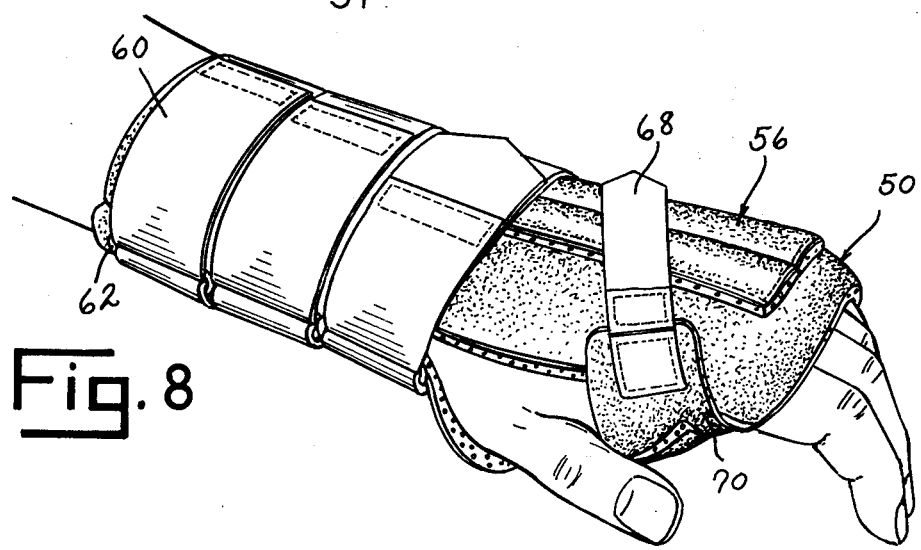
FIG. 8 is a perspective view of the wrist immobilizer shown applied about the wrist of a patient.

The immobilizer shown in FIGS. 6–8 includes a flexible cover 50 having looped pile material 52 applied to its outer surface. A pair of stays 54 and 56 are connected to cover 50. Stay 56 is detachable and includes an encasement 58 to which a plurality of hooks 59 are attached to one side. Stay 54 is preferably sewn to cover 50 but if desired can be of a similar detachable construction as stay 56. Stay 56 carries straps 60 and stay 54 carries rings 62 for securing the immobilizer about the wrist of the patient as shown in FIG. 8 with the straps being inserted through the rings and return bent to have hook 64 carried by the straps pressed into locking engagement with pile material 66 extending along the straps.

Strap 68 of hook material serves to secure tab 70 about the hand of the patient. The hooks 59 of stay 56 allow the stay to be pressed into interlocking engagement with cover material 52 and selectively located to accommodate the wrist of the patient.

Figure 9:
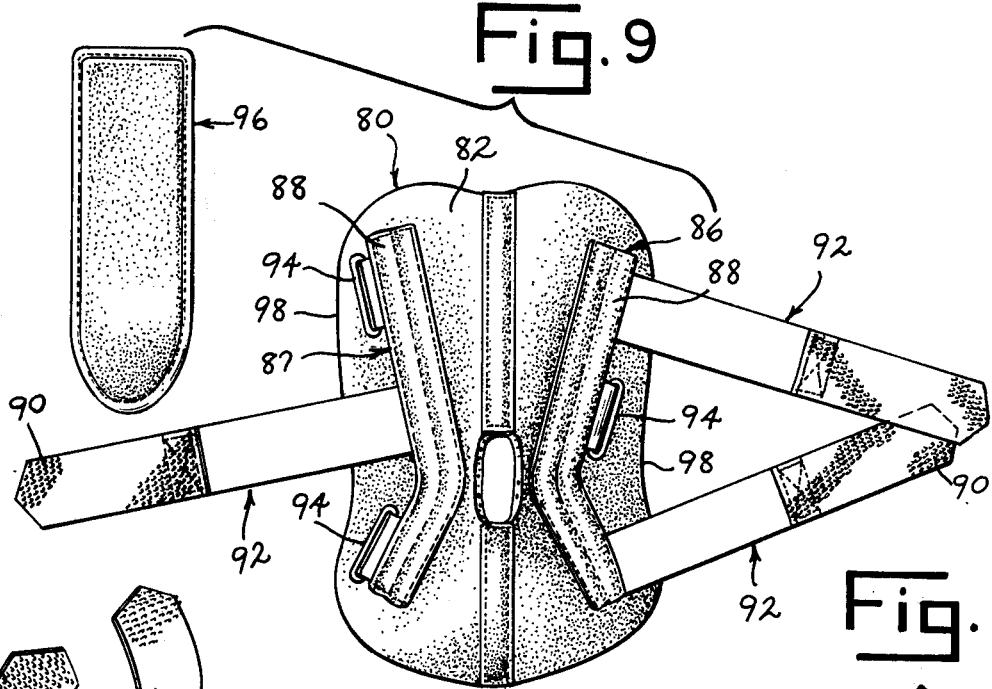
FIG. 9 is a plan view of an ankle immobilizer shown with the fore stay pad detached.
Figure 10:
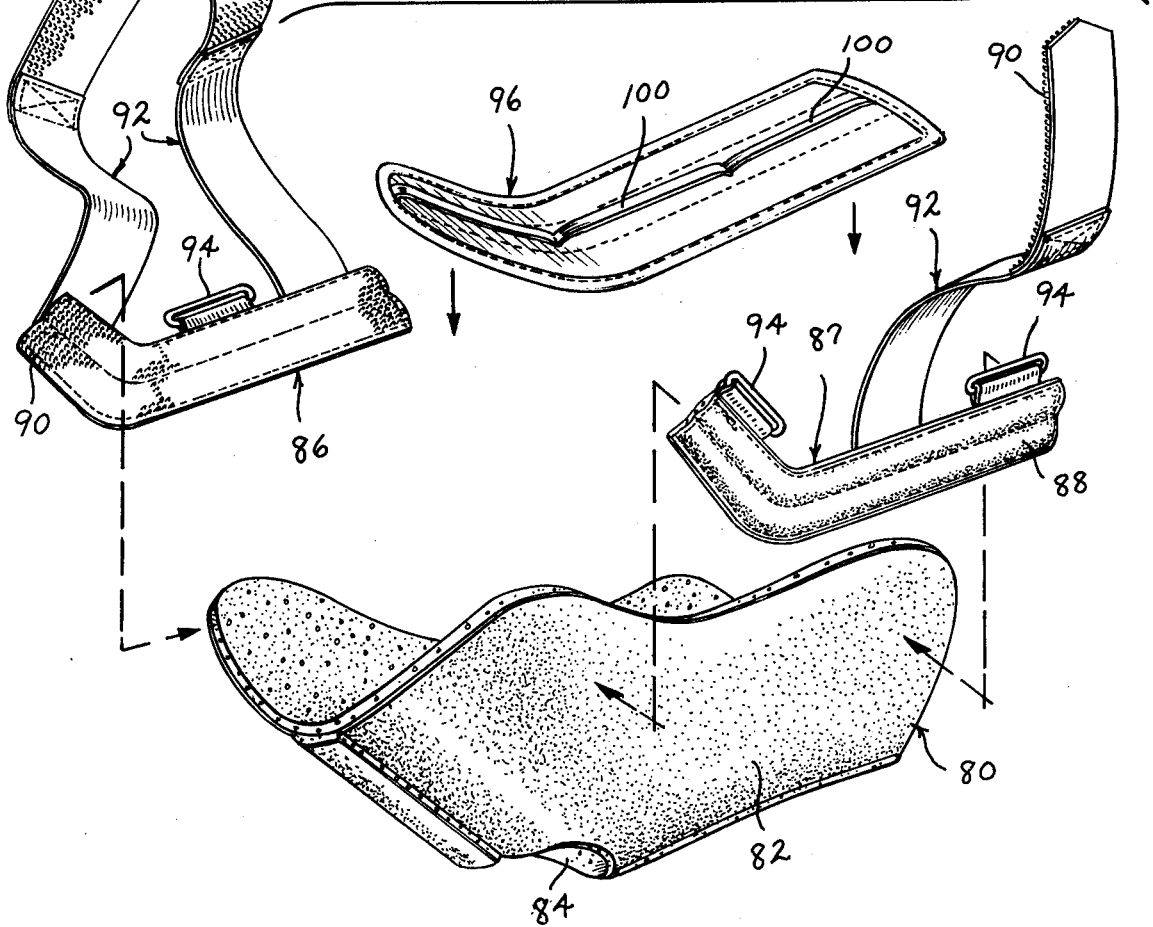
FIG. 10 is a perspective view of the ankle immobilizer showing the stays and fore stay pad detached from the immobilizer.
Figure 11:
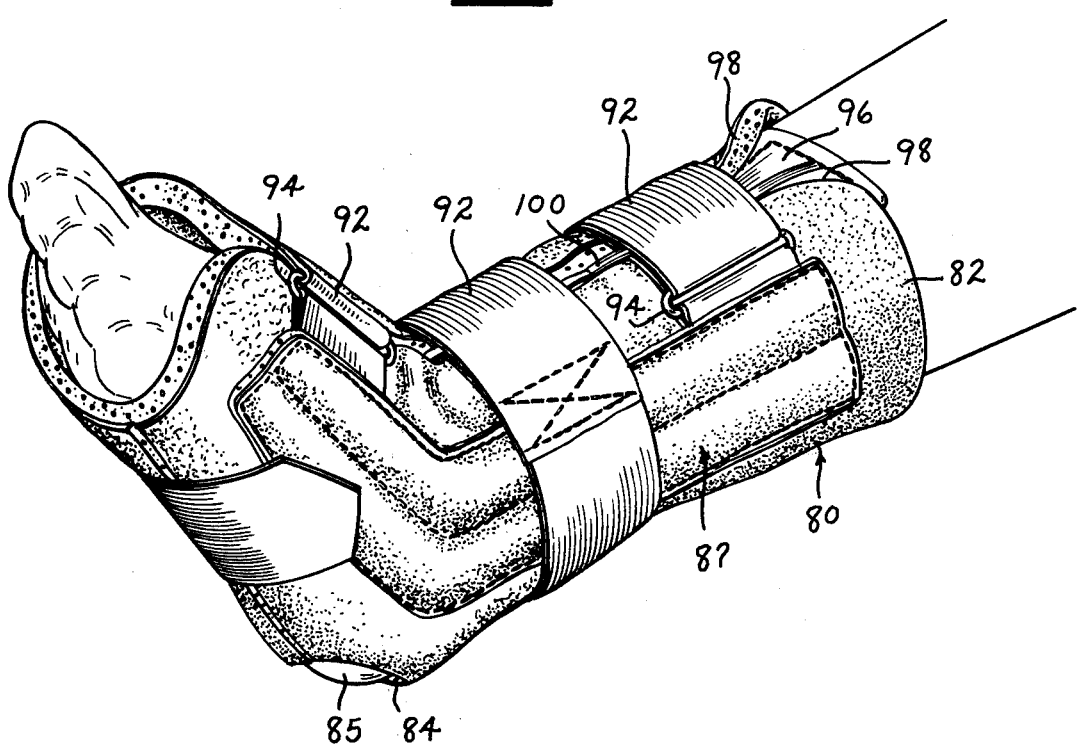
FIG. 11 is a perspective view of the ankle immobilizer shown applied about the ankle of a patient.

The immobilizer shown in FIGS. 9–11 includes a cover 80 having looped pile material 82 applied to its outer surface. Cover 80 has a center opening 84 to accommodate the heel 85 of the patient. A pair of detachable stays 86 and 87 are connected to cover 80 and located at the inside and outside of the foot when the immobilizer is applied to the patient's ankle. Stays 86 and 87 are bent to a desired anatomical configuration and each includes an encasement 88 to which a plurality of hooks 90 are attached to one side. Each stay carries one or more straps 92 and one or more rings 94 for securing the immobilizer about the ankle of the patient as shown in FIG. 11. A fore stay pad 96 is applied over the front of the ankle with side edges 98 of cover 80 preferably overlapping the pad and straps 92 passing through loops 100 of the pad.

Straps 92 are also inserted through rings 94 and return bent with the hooks 90 carried by the straps being pressed into interlocking engagement with material 82 of the cover and similar material forming the outer side of stay encasements 88.

In the wrist and ankle immobilizer embodiments of FIGS. 6–11, pile material 52 and 82 and hooks 59 and 90 may be of the cooperating interlocking type sold under the trademark "Velcro." It is to be understood that the invention may be applied to various types of body part immobilizers and is not to be limited to the details above given but may be modified within the scope of the appended claims.

What I claim is:

1. An immobilizer for a body part of a patient comprising a flexible cover means having in planar orientation upper and lower edges and opposite side edges, said cover means including an outer surface formed of loop means, rigidifying means, said rigidifying means including hook means for detachable and adjustable securement to said cover means at the loop means thereof, and means for securing said cover means about said body part, said rigidifying means being adjustably secured to said cover means adjacent one said cover means side edge with the hook means of the rigidifying means interlocking with the loop means of the cover means for positioning along said body part when said cover means is applied to the patient.

2. The immobilizer of claim 1 wherein said rigidifying means includes an encasement part enclosing a stay component with said hook means forming a portion of the encasement part.

3. The immobilizer of claim 1 wherein said cover securing means includes a strap anchored to said cover means.

4. The immobilizer of claim 3 wherein said strap is carried by said rigidifying means.

5. The immobilizer of claim 4 and a second rigidifying means secured to said cover means adjacent the other said cover means side edge.

6. The immobilizer of claim 5 wherein said second rigidifying means has hook means for detachable and adjustable securement to said cover means, said second rigidifying means being adjustably secured to said cover means with the hook means for the second rigidifying means interlocking with the loop means of the cover means for positioning along said body part when the cover means is applied to the patient.

7. The immobilizer of claim 6 wherein at least one of said rigidifying means is bent to follow the anatomical curvature of said body part.

8. The immobilizer of claim 6 wherein said cover securing means includes parts carried by said second rigidifying means which are cooperable with said strap.

9. An immobilizer for a body part of a patient comprising a flexible cover means having in a generally planar orientation upper and lower edges and opposite side edges, said cover means including an outer surface formed of loop means, rigidifying means, said rigidifying means including hook means for detachable and adjustable securement to said cover means at the loop means thereof, and means for securing said cover means about said body part, said rigidifying means being adjustably secured to said cover means with the hook means of the rigidifying means interlocking with the loop means of the cover means for positioning over said body part when said cover means is applied to the patient.

10. The immobilizer of claim 9 wherein said cover securing means includes a strap anchored to said cover means.

11. The immobilizer of claim 10 wherein said strap is carried by said rigidifying means.

* * * * *